US012788243B2

(12) United States Patent
Mita et al.

(10) Patent No.: US 12,788,243 B2
(45) Date of Patent: Nov. 10, 2026

(54) OPHTHALMIC DEVICE

(71) Applicant: NIDEK CO., LTD., Aichi (JP)

(72) Inventors: Shinji Mita, Gamagori (JP); Seiji Masegi, Gamagori (JP); Ryo Nakamura, Gamagori (JP)

(73) Assignee: NIDEK CO., LTD., Aichi (JP)

( * ) Notice: Subject to any disclaimer, the term of this patent is extended or adjusted under 35 U.S.C. 154(b) by 168 days.

(21) Appl. No.: 19/001,346

(22) Filed: Dec. 24, 2024

(65) Prior Publication Data

US 2025/0275677 A1 Sep. 4, 2025

(30) Foreign Application Priority Data

Mar. 4, 2024 (JP) ................................ 2024-032074

(51) Int. Cl.
*A61B 3/107* (2006.01)
*A61B 3/00* (2006.01)
*A61B 3/15* (2006.01)

(52) U.S. Cl.
CPC ............ *A61B 3/107* (2013.01); *A61B 3/0025* (2013.01); *A61B 3/0091* (2013.01); *A61B 3/152* (2013.01)

(58) Field of Classification Search
USPC ........................................................ 351/212
See application file for complete search history.

(56) References Cited

U.S. PATENT DOCUMENTS

| | | | | | |
|---|---|---|---|---|---|
| 5,302,979 | A * | 4/1994 | Maeda | A61B 3/107 | 351/212 |
| 5,625,428 | A * | 4/1997 | Isogai | A61B 3/107 | 351/208 |
| 2011/0075098 | A1* | 3/2011 | Endo | A61B 3/107 | 351/212 |
| 2013/0050643 | A1* | 2/2013 | Endo | A61B 3/14 | 351/246 |
| 2023/0148857 | A1* | 5/2023 | Neal | G16H 40/67 | 351/219 |

FOREIGN PATENT DOCUMENTS

JP 2000279383 10/2000

* cited by examiner

*Primary Examiner* — Mohammed A Hasan
(74) *Attorney, Agent, or Firm* — JCIPRNET

(57) ABSTRACT

An ophthalmic device for measuring a cornea shape of an examinee's eye includes a measurement pattern index plate on which a pattern index for measuring the cornea shape of the examinee's eye is formed, and a surface light emitting panel in a flat plate shape that illuminates the measurement pattern index plate from behind to project the pattern index onto the cornea of the examinee's eye. The surface light emitting panel includes a light guide plate that guides light, an illuminating light source configured at an end portion of the light guide plate, and a reflection pattern configured on a back surface side of the light guide plate to reflect light from the illuminating light source to a front surface side of the light guide plate. A density of the reflection pattern is adjusted corresponding to a positional relationship between the surface light emitting panel and the pattern index.

6 Claims, 5 Drawing Sheets

OPHTHALMIC DEVICE

CROSS-REFERENCE TO RELATED APPLICATION

This application claims the priority benefits of Japanese application no. 2024-032074, filed on Mar. 4, 2024. The entirety of the above-mentioned patent application is hereby incorporated by reference herein and made a part of this specification.

BACKGROUND

Technical Field

The disclosure relates to an ophthalmic device that measures a cornea shape of an examinee's eye.

Description of Related Art

An ophthalmic device is known that projects a pattern index (for example, a plurality of ring pattern indices) onto the cornea of an examinee's eye for measuring the cornea shape, and measures the detailed cornea shape by capturing an index image formed on the cornea. In this type of ophthalmic device, an illumination unit is provided that illuminates an index plate, in which light-transmitting portions and light shielding portions are alternately formed, from behind.

As a conventional illumination unit, for example, a configuration has been proposed in which a pattern index is illuminated from behind by surface light emission of a surface light emitting plate (refer to Patent Document 1, Japanese Patent Publication No. 2000-279383).

However, further improvements are desired in the projection of pattern indices for measuring cornea shape. For example, in the configuration of Patent Document 1, there is a configuration such that the surface light emitting plate is formed in a substantially spherical shape with the pattern index portion integrally formed on the surface of the surface light emitting plate, or a configuration using two conical surface light emitting plates behind the pattern index plate, making the shape of the surface light emitting plate complex and difficult to manufacture. Further, Patent Document 1 discloses a configuration where a plurality of surface light emitting plates in a flat plate shape are divided and configured behind a hemispherical pattern index plate, but there is a problem that it is difficult to uniformly illuminate the pattern index if the position of the pattern index plate relative to the surface light emitting plates differs depending on the location.

The disclosure, in view of the above conventional technology, provides an ophthalmic device that may illuminate a pattern index more uniformly without complicating the configuration as a technical challenge.

SUMMARY

An ophthalmic device provided by a typical embodiment of the disclosure is an ophthalmic device for measuring a cornea shape of an examinee's eye, including: a surface light emitting panel in a flat plate shape, including a light guide plate in a flat plate shape and an illuminating light source, the light guide plate having a back surface on which a reflection pattern is formed to reflect illumination light guided inside and a front surface from which the illumination light reflected by the reflection pattern is emitted, and the illuminating light source being configured on a side surface of the light guide plate to irradiate the illumination light inside the light guide plate; an index plate, on which a measurement pattern is formed and forming a pattern index to be projected onto a cornea of an examinee's eye by passing illumination light from the surface light emitting panel through the measurement pattern; an imaging optical system, capturing an index image which is a cornea reflection image of the pattern index; and an image processor, obtaining information related to a cornea shape of an examinee's eye by performing analysis processing on the index image. A density of the reflection pattern at each position of the surface light emitting panel is adjusted corresponding to a positional relationship between the surface light emitting panel and the measurement pattern.

DESCRIPTION OF THE EMBODIMENTS

Figure 1:
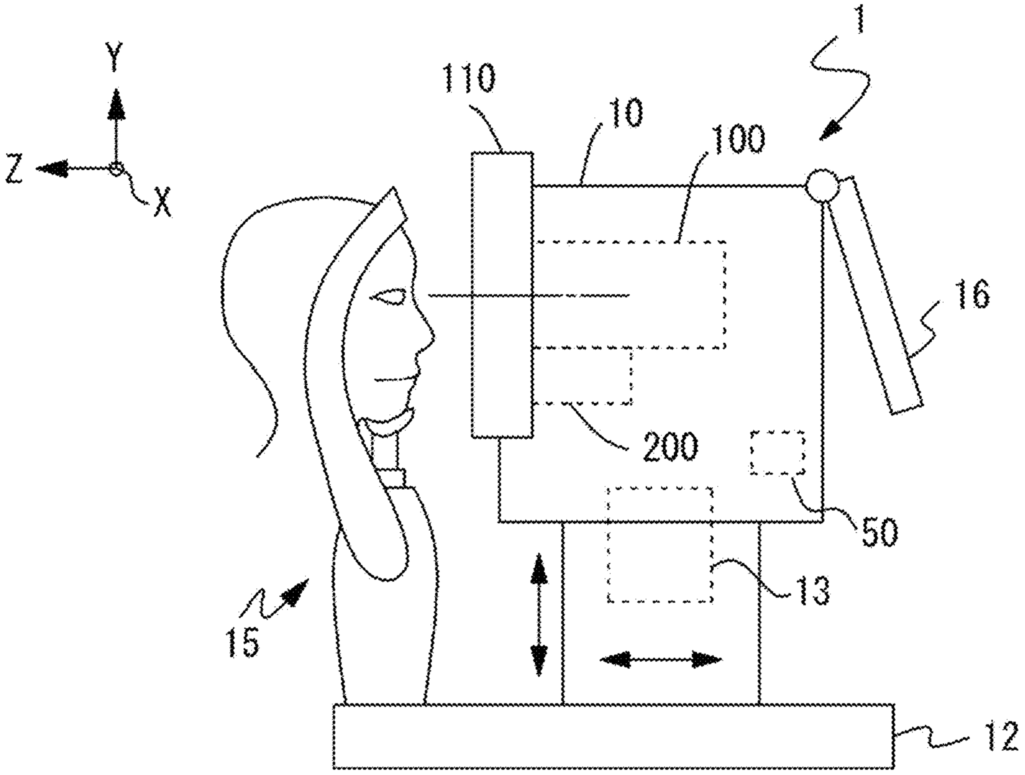
FIG. 1 is an external view of the ophthalmic device.

The following describes one typical embodiment with reference to the drawings. It is noted that the items classified in the following < > may be used independently or in relation to each other.

The ophthalmic device of the disclosure (for example, ophthalmic device 1) includes an index projection unit (for example, index projection unit 110), an imaging optical system (for example, front imaging optical system 150), and an image processor (for example, controller 50). The index projection unit projects a pattern index onto the cornea of an examinee's eye. The imaging optical system captures an index image, which is a cornea reflection image of the pattern index. The image processor (for example, the controller 50) obtains information related to the cornea shape of the examinee's eye by performing analysis processing on the index image captured by the imaging optical system.

The index projection unit includes an index plate (for example, index plate 120) and a surface light emitting panel (for example, surface light emitting panel 130).

For example, a measurement pattern (for example, measurement pattern 122) is formed on the index plate. The pattern index projected onto the cornea of the examinee's eye is formed by the index plate as the illumination light from the surface light emitting panel, which is described later, passes through the measurement pattern.

It is noted that the measurement pattern may be, for example, a multiplex ring pattern. Further, it may also be another two-dimensional pattern formed by lines or a plurality of points. For example, a plurality of point images configured two-dimensionally may be projected as the pattern index. Further, a plurality of patterns may be combined.

For example, the index plate may have an inclined portion (for example, inclined portion 121B) that is inclined with respect to the surface light emitting panel. For example, the index plate may include a flat portion (for example, flat portion 121A) centered on the photographic optical axis. In this case, the inclined portion is configured on the outer peripheral side of the flat portion. Further, the surface light emitting panel is configured parallel to the flat portion. The shape of the index plate is not necessarily limited thereto. For example, the entire index plate may be substantially spherical. In this case, almost the entire index plate may be the inclined portion.

In the case where the index plate has an inclined portion, a reflective plate (for example, reflective plate 140) may be configured on the outer peripheral side of the inclined portion. The reflective plate reflects the illumination light emitted from the surface light emitting panel, thereby guiding the illumination light to the measurement pattern formed on the inclined portion. By providing the reflective plate, the measurement pattern may be efficiently illuminated. Further, it becomes easier to miniaturize the surface light emitting panel and the entire device.

The surface light emitting panel illuminates the index plate from behind. In this embodiment, the surface light emitting panel is formed in a flat plate shape. For example, the front surface and the back surface of the surface light emitting panel are substantially perpendicular to the photographic optical axis of the imaging optical system. Since the surface light emitting panel is formed in a flat plate shape, it is easier to manufacture and simplify the structure compared to cases where it is hemispherical or conical.

For example, the surface light emitting panel includes a light guide plate (for example, light guide plate 131), an illuminating light source (for example, illuminating light source 132), and a reflection pattern (for example, reflection pattern 133). The light guide plate is formed in a flat plate shape. The illuminating light source is configured at the end portion (side surface) of the light guide plate. The illumination light from the illuminating light source is guided inside the light guide plate. The reflection pattern is configured on the back surface of the light guide plate. The illumination light guided inside is reflected by the reflection pattern. The illumination light reflected by the reflection pattern is emitted from the front surface of the light guide plate. Furthermore, the surface light emitting panel may include a reflective sheet (for example, reflective sheet 134) and a diffusion plate (for example, diffusion plate 135). For example, the reflective sheet is configured on the back surface of the surface light emitting panel, sandwiching the reflection pattern. For example, the diffusion plate diffuses the illumination light emitted from the front surface of the light guide plate.

For example, the reflection pattern may be a dot pattern consisting of a plurality of reflection dots. The reflection dots in the dot pattern may be formed, for example, by printing a paint with reflective characteristics in a dot shape on the back surface of the light guide plate. However, the reflection pattern is not necessarily limited to the dot pattern. For example, grooves or scratches may be formed on the back surface of the light guide plate as the reflection pattern. In this case, the grooves or scratches may be formed by a plotter or laser, etc. Further, the light guide plate and the reflection pattern may be integrally molded by forming protrusions and depressions that form the reflection pattern in the resin mold of the light guide plate.

For example, the density of the reflection pattern at each position of the surface light emitting panel (light guide plate) is adjusted corresponding to the positional relationship between the surface light emitting panel and the measurement pattern. This allows the pattern index to be projected onto the cornea with uniform light intensity while simplifying the structure of the index projection unit.

Furthermore, the density of the reflection pattern may also be adjusted corresponding to the positional relationship between the reflection pattern and the illuminating light source. For example, the amount of light guided by the light guide plate decreases as the distance from the illuminating light source increases. In response to this, the density of the reflection pattern may be adjusted to become denser as it gets farther from the illuminating light source.

Further, at least one of the reflection pattern in the surface light emitting panel (light guide plate) and the measurement pattern in the index plate may be formed based on the photographic optical axis of the imaging optical system. For example, the reflection pattern may be distributed so that illumination light is emitted uniformly from each position on the front surface of the surface light emitting panel. However, instead of such a distribution, the reflection pattern may be distributed so that the reflection pattern becomes denser with increasing distance from the photographic optical axis. In this case, the farther the position is from the photographic optical axis, the greater the amount of light emitted from the surface light emitting panel. As a result, it becomes easier to uniformize the light intensity of the pattern index on the cornea of the examinee's eye.

Specifically, the inclination of the light beams (the angle of inclination with respect to the vertical direction of the surface light emitting panel) that contribute to the formation of the pattern index image increases as the distance from the photographic optical axis increases. Thus, even if the light intensity is uniform across the entire front surface when viewed from the front direction of the surface light emitting panel (vertical direction of the surface light emitting panel), the light intensity of the light beams contributing to the formation of the pattern index image far from the photographic optical axis does not become the same as the light intensity near the photographic optical axis, and becomes weaker as it gets farther from the optical axis. Consequently, as mentioned above, in contrast to the density of the reflection pattern adjusted so that the illumination intensity emitted from the entire front surface of the surface light emitting panel is uniform, the density of the reflection pattern may be adjusted to become denser as it gets farther from the photographic optical axis of the imaging optical system.

For example, in the case where the index plate includes a flat portion centered on the photographic optical axis and an inclined portion is configured on the outer peripheral side of the flat portion, in the case where the illumination intensity on the front surface of the surface light emitting panel is uniform across the entire front surface, due to the diffuse reflection of the reflective plate, the illumination intensity tends to be stronger on the inclined portion than on the flat portion of the index plate. Thus, the configuration density of the reflection pattern may be adjusted so that the illumination intensity on the inclined portion becomes weaker. For example, the density of the reflection pattern may be adjusted so that the illumination intensity on the front surface of the surface light emitting panel corresponding to the measurement pattern formed on the inclined portion becomes relatively weaker compared to the illumination intensity on the front surface of the surface light emitting panel corresponding to the flat portion. By doing so, in the case of a configuration where the reflective plate is configured on the outer peripheral side of the inclined portion, both the measurement pattern on the flat portion and the measurement pattern on the inclined portion of the index plate may be uniformly illuminated with approximately the same light intensity.

Further, for example, the ophthalmic device may include, as an optical system, in addition to the optical system for cornea shape measurement, an alignment optical system (for example, working distance detection optical system 160, anterior ocular segment illuminating light source 155) having an optical axis inclined with respect to the imaging optical system and used for alignment of the imaging optical system with respect to the examinee's eye. For example, the ophthalmic device may additionally include, in addition to the optical system for cornea shape measurement, an optical system (for example, cross-sectional imaging optical system 210) having an optical axis different from the optical axis of the imaging optical system and used for measuring optical characteristics of the examinee's eye. In this case, the surface light emitting panel may have a light passing hole (for example, light passing holes 134*a*, 134*b*, 134*c*) formed to allow at least one of a light beam used for alignment or a light beam used for measuring optical characteristics of the examinee's eye other than the cornea shape measurement to pass through. Then, in this case, the density of the reflection pattern of the surface light emitting panel may be adjusted according to the formation position of the light passing hole. For example, compared to the case where no light passing hole is configured, in the case where a light passing hole is configured, the density of the reflection pattern is made relatively higher. By doing so, even in the case where a light passing hole is formed in the surface light emitting panel, the influence (for example, the influence of attenuation of illumination light from the illuminating light source provided at the end portion of the surface light emitting panel due to the presence of the light passing hole) may be suppressed, and regardless of the formation position of the light passing hole, the measurement pattern formed on the index plate may be uniformly illuminated.

Further, for example, when viewed from the front direction where the examinee's eye is positioned, the surface light emitting panel may be formed into a polygon with more sides than a quadrilateral, corresponding to the shape of the index plate. For example, the surface light emitting panel may be formed into a polygon with eight or more sides. Then, the illuminating light source provided on the surface light emitting panel may be configured on each side of the polygon. By doing so, compared to the case where the surface light emitting panel is quadrilateral, the index plate may be efficiently illuminated from behind with reduced illumination unevenness. It is noted that the index plate may have an elongated shape that is longer in the left and right direction, and correspondingly, the surface light emitting panel may also have an elongated shape. For example, when viewed from the front direction where the examinee's eye is positioned, the index plate may have a shape where the length in the longitudinal direction gradually decreases towards the end portions in each of the left and right directions with respect to the longitudinal direction of the center portion, and the surface light emitting panel, when viewed from the front direction where the examinee's eye is positioned, may have an elongated shape that is longer in the left and right direction corresponding to the shape of the index plate.

EXAMPLE

<Overall Configuration>

An example of this embodiment is described based on the drawings. FIG. 1 is an external view of the ophthalmic device 1. The ophthalmic device 1 includes an optometry unit 10, a base 12, an alignment driving portion 13, a face supporting unit 15, a monitor 16, and a controller 50. The optometry unit 10 includes a cornea shape measurement portion 100 for measuring the cornea shape of the examinee's eye (E). An index projection unit 110 of the cornea shape measurement portion 100 is configured on the front side (examinee's eye side) of the optometry unit 10. The index projection unit 110 is configured facing the examinee's eye. It is noted that the ophthalmic device 1 may have an examination portion other than the cornea shape measurement portion 100 for examining (measuring or imaging) optical characteristics of the examinee's eye other than the cornea shape measurement. In this example, an example where the optometry unit 10 is provided with an anterior ocular segment cross-sectional imaging portion 200 (refer to FIG. 2) is described.

The alignment driving portion 13 changes the positional relationship of the optometry unit 10 with respect to the examinee's eye. For example, the alignment driving portion 13 moves the optometry unit 10 three-dimensionally with respect to the base 12, thereby moving the optometry unit 10 in the X direction (left and right direction), Y direction (up and down direction), and Z direction (front and rear direction) with respect to the examinee's eye. The face supporting unit 15 is used to fix the face of the examinee in front of the optometry unit 10. The face supporting unit 15 is fixed to the base 12 and fixes the examinee's eye by supporting the face of the examinee.

<Optical System>

Figure 2:
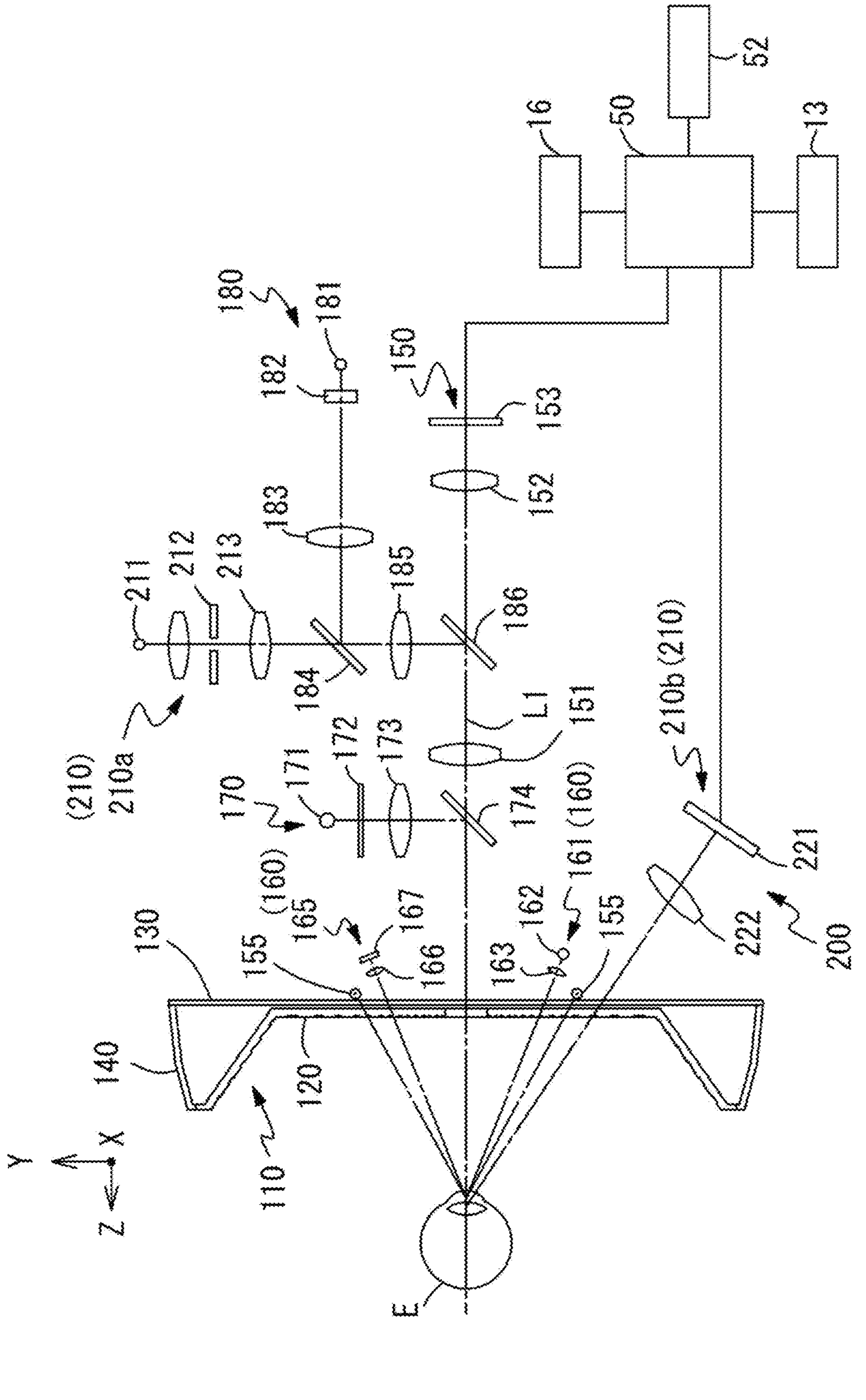
FIG. 2 is a schematic configuration view of an optical system configured in the optometry unit and a control system of the ophthalmic device.

FIG. 2 is a schematic configuration view of the optical system configured in the optometry unit 10 and the control system of the ophthalmic device 1. The cornea shape measurement portion 100 includes an index projection unit 110 for measuring the cornea shape of the examinee's eye (E), a front imaging optical system 150, a working distance detection optical system 160, a front alignment index projection optical system 170, and a fixation target presentation optical system 180. Further, the anterior ocular segment cross-sectional imaging portion 200 includes a cross-sectional imaging optical system 210.

<Index Projection Unit>

The index projection unit 110 includes an index plate 120 and a surface light emitting panel 130. The surface light emitting panel 130 is configured behind the index plate 120. Further, the index projection unit 110 may optionally include a reflective plate 140 on the outer peripheral portion of the index plate 120.

<Index Plate>

Figure 3A:
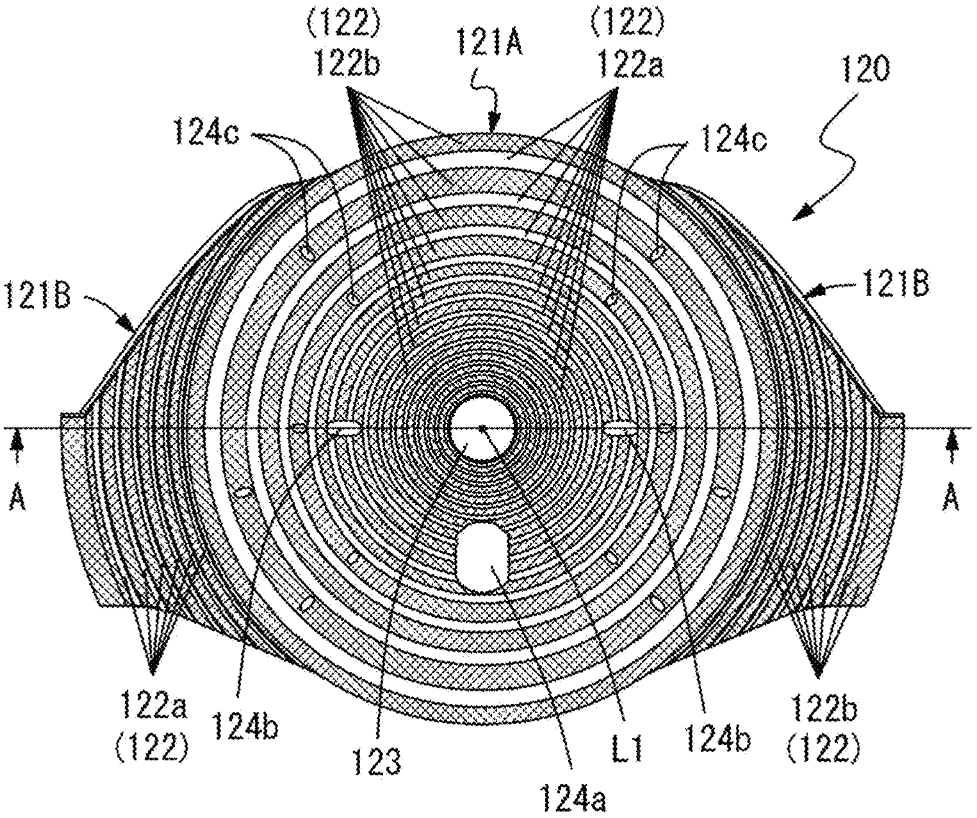
FIG. 3A and FIG. 3B are views describing the configuration of the index plate.
Figure 3B:
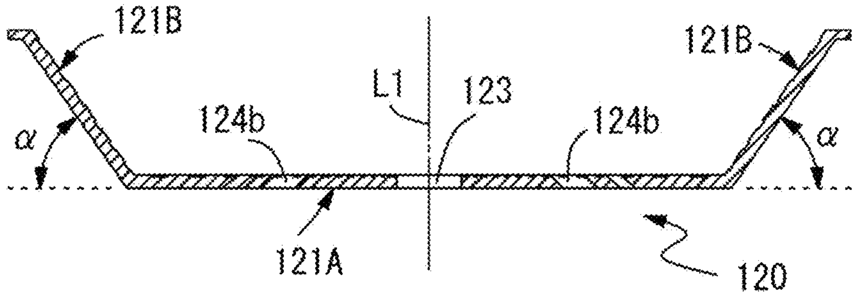

FIG. 3A and FIG. 3B are views describing the configuration of the index plate 120. FIG. 3A is a view of the index plate 120 from the front direction on the side where the examinee's eye is positioned, and FIG. 3B is an A-A cross-sectional view of FIG. 3A.

The index plate 120 is composed of a light guide plate 120*a* (for example, acrylic resin) that guides illumination light from the surface light emitting panel 130. On the front surface side of the index plate 120, a measurement pattern 122 for measuring the cornea shape is formed. The back surface of the index plate 120 may be a diffusion surface that diffuses light entering the interior of the light guide plate 120*a*.

The index plate 120 includes a flat portion 121A in a flat plate shape and inclined portions 121B configured on the outer peripheral side of the flat portion 121A. The flat portion 121A includes a center opening 123 through which the optical axis L1 of the front imaging optical system 150 passes, and is formed in a circular shape around the entire circumference with the center of the center opening 123 as a reference, and a ring-shaped measurement pattern 122 is formed on almost the entire front surface of the flat portion 121A.

The inclined portions 121B are configured on the outer peripheral side of the flat portion 121A and are formed in a conical shape or curved shape with the center of the center opening 123 as a reference. In this example, when viewing the index plate 120 from the front direction (examinee's eye side), the inclined portions 121B are formed on the left and right sides of the circular-shaped flat portion 121A. In the example of FIG. 3A and FIG. 3B, the inclined portions 121B have a length in the longitudinal direction that gradually or stepwise decreases with increasing distance from the flat portion 121A.

For example, the measurement pattern 122 on the flat portion 121A is designed to measure the shape within a diameter of 8 mm for a standard examinee's eye cornea. In other words, in the range of 8 mm diameter of the cornea where the measurement of the cornea shape is emphasized, the ring-shaped measurement pattern 122 is designed to be formed on almost the entire front surface. On the other hand, the measurement pattern 122 of the inclined portion 121B is designed to measure the shape within the range up to 10 to 11 mm diameter for a standard examinee's eye cornea. In the ophthalmic device 1 of this example, to avoid enlarging the index projection unit 110 in the up and down direction, the inclined portion 121B is not provided in the longitudinal direction (up and down direction) at the center of the flat portion 121A. This is because in the up and down direction of the examinee's eye, the light beam is easily vignetted by the eyelids and cheeks, so the impact of the absence of the inclined portion 121B in the longitudinal direction is minimal.

For example, the inclination angle α of the inclined portion 121B (the inclination angle relative to the surface light emitting panel 130 configured parallel to the flat portion 121A) is set to 40 to 70 degrees. In this example, the inclination angle α is set to 55 degrees. In the case where the inclination angle α is greater than 70 degrees, the depth of field is necessary to be increased when capturing the index image by the front imaging optical system 150 (in order to obtain an index image that is as focused as possible), which tends to be disadvantageous in obtaining a high-quality captured image. In the case where the inclination angle α is less than 45 degrees, the overall external shape of the index plate 120 becomes larger, which tends to be disadvantageous in the use of the device.

It is noted that the index plate 120 may be in a hemispherical shape. In this case, the inclination angle of the inclined portion 121B is not constant, but changes to gradually increase.

In this example, the measurement pattern 122 forms a ring-shaped pattern index. For example, the measurement pattern 122 is configured by forming light-transmitting portions 122*a* that transmit illumination light from the surface light emitting panel 130 and light shielding portions 122*b* that block illumination light from the surface light emitting panel 130 on the index plate 120. The light-transmitting portions 122*a* and the light shielding portions 122*b* are formed alternately in a plurality of concentric circles centered on the optical axis L1. By illuminating the index plate 120 with the surface light emitting panel 130 behind it, a so-called Placido ring pattern is projected onto the cornea of the examinee's eye as a pattern index.

It is noted that light passing holes 124*a*, 124*b*, and 124*c* are formed on the index plate 120 outside the center opening 123. The light passing hole 124*a* allows the light beam of the cross-sectional imaging optical system 210 to pass through. The light passing holes 124*b* allow the light beam of the working distance detection optical system 160 to pass through. The light passing holes 124*c* allow illumination light (light beam from the anterior ocular segment illuminating light source 155 to be described later) for illuminating the examinee's eye during alignment and observation of the examinee's eye to pass through. In the example of FIG. 3A and FIG. 3B, the light passing hole 124*a* is formed below the center opening 123. The light passing holes 124*b* are formed at two locations in the left and right direction centered on the optical axis L1. The light passing holes 124*c* are formed at six locations on the first concentric circle outside the light passing holes 124*b* centered on the optical axis L1, at 0 degrees, 45 degrees, 135 degrees, 180 degrees, 225 degrees, and 315 degrees directions, and also formed at six locations on the second concentric circle outside the first concentric circle, at 45 degrees, 135 degrees, 195 degrees, 225 degrees, 315 degrees, and 345 degrees directions.

<Surface Light Emitting Panel>

Figure 4:
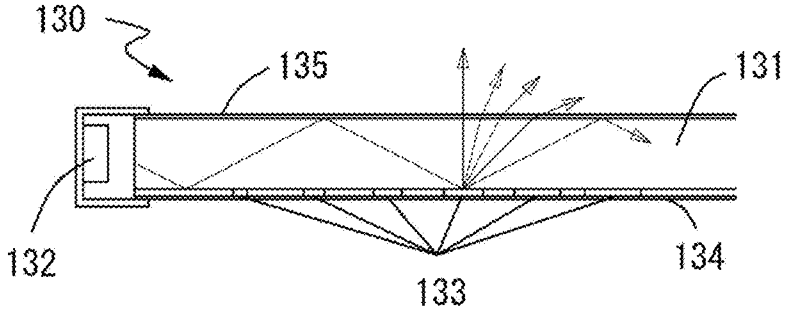
FIG. 4 is a view describing the configuration of the surface light emitting panel and is a partial cross-sectional view of the surface light emitting panel.
Figure 5:
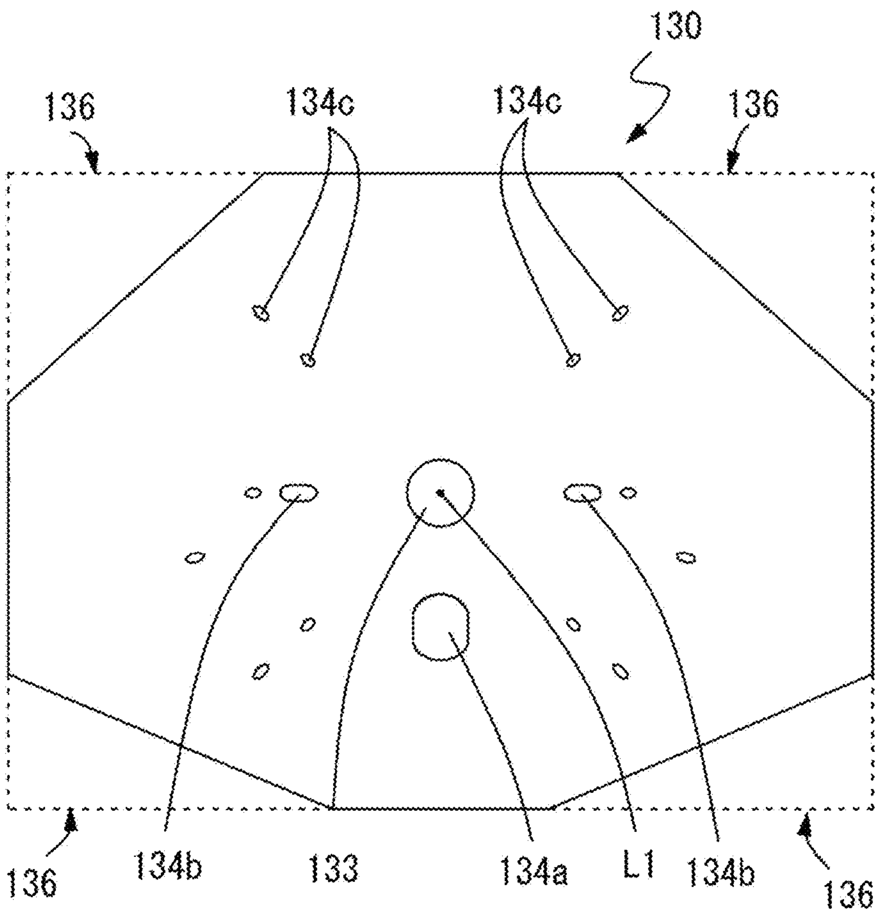
FIG. 5 is a view describing the configuration of the surface light emitting panel and is a view of the surface light emitting panel as viewed from the front direction.

The surface light emitting panel 130 is used to illuminate the index plate 120 from behind to project the pattern index onto the cornea of the examinee's eye. The surface light emitting panel 130 is configured in a direction perpendicular to the photographic optical axis L1 of the front imaging optical system 150. FIG. 4 is a view describing the configuration of the surface light emitting panel 130 and is a partial cross-sectional view of the surface light emitting panel 130. FIG. 5 is a view describing the configuration of the surface light emitting panel 130 and is a view of the surface light emitting panel 130 from the front direction on the side where the examinee's eye is positioned. It is noted that the surface light emitting panel 130 is formed in a flat plate shape, as opposed to being formed in a hemispherical or conical shape, which facilitates its manufacture and allows the configuration of the surface light emitting panel 130 to remain uncomplicated.

In FIG. 4, the surface light emitting panel 130 is primarily composed of a light guide plate 131, an illuminating light source 132, a reflection pattern 133, a reflective sheet 134, and a diffusion plate 135. The light guide plate 131 is a plate of light-transmitting material.

For example, the light guide plate 131 is composed of a transparent resin body such as acrylic. The illuminating light source 132 is composed of a LED or the like that emits visible light.

The illuminating light source 132 is configured with a plurality of units placed in a row at the end portion of the light guide plate 131. The reflection pattern 133 is formed by reflection dots, which are paint with reflective characteristics printed in a dot pattern on the back surface of the light guide plate 131.

The reflection pattern 133 may also be a groove pattern formed by creating grooves in the light guide plate 131 using a plotter, a scratch pattern created by laser light, or a molded pattern formed by pouring resin such as acrylic into a mold, in addition to the reflection dot pattern created by printing. The illumination intensity emitted from the front surface of the surface light emitting panel 130 may be altered by adjusting the density (distribution density) of the reflection pattern 133. It is noted that in FIG. 4, the reflection pattern 133 is schematically illustrated. For example, in the case where the reflection pattern 133 is a reflection dot pattern, reflection dots of the same size are formed in a distributed manner, and in the case of increasing the density of the reflection pattern 133, it is formed such that the intervals between each reflection dot become narrower.

The reflective sheet 134 is configured on the back surface of the surface light emitting panel 130, sandwiching the reflection pattern 133. This allows the light from the illuminating light source 132 guided by the light guide plate 131 to be reflected towards the front surface side. The diffusion plate 135 is configured on the front surface side of the surface light emitting panel 130 and diffuses the light emitted from the front surface of the surface light emitting panel 130.

It is noted that in FIG. 4, the manner of light emitted from the illuminating light source 132 propagating through internal reflection in the light guide plate 131, and the manner in which it emits from the front surface of the surface light emitting panel 130 are additionally illustrated.

Here, the reflection pattern 133 is formed with its density (in the case of reflection dots, the density of dot configuration) adjusted corresponding to the positional relationship between the reflection pattern 133 and the illuminating light source 132. The light emitted from the illuminating light source 132 is also guided to a distant reflection pattern 133 by internal reflection in the light guide plate 131. However, as the distance from the illuminating light source 132 increases, the light attenuates. Thus, for example, in the case where uniform illumination intensity is desired from the front surface of the surface light emitting panel 130, the density of the reflection pattern 133 is adjusted to become denser as the distance from the illuminating light source 132 increases.

In FIG. 5, the external shape of the surface light emitting panel 130 is formed as a polygon with more sides than a quadrilateral, corresponding to the shape of the index plate 120. The illuminating light source 132 is configured on each side of the polygon. In this example, the surface light emitting panel 130 is formed as an octagon.

In this case, in the case where the surface light emitting panel 130 were rectangular as indicated by the dotted line in FIG. 5, the light-emitting parts at the four corners of the dotted line parts 136 would be far from the index plate 120, resulting in wasted illumination light. Further, this may lead to the possibility of illumination unevenness occurring on the index plate 120.

In contrast, the surface light emitting panel 130 in the example of the disclosure is formed as an octagon, eliminating the waste of the dotted line parts 136, thereby allowing efficient illumination of the index plate 120 while reducing illumination unevenness.

Further, as shown in FIG. 5, the surface light emitting panel 130 includes, besides the center opening 133 through which the light beam for cornea shape measurement passes, a light passing hole 134*a* through which the light beam of the cross-sectional imaging optical system 210 passes, light passing holes 134*b* through which the light beam of the working distance detection optical system 160 passes, and light passing holes 134*c* through which illumination light for illuminating the examinee's eye during alignment and observation of the examinee's eye passes, similar to the index plate 120. The configuration positions and number of the light passing hole 134*a*, the light passing hole 134*b*, and the light passing hole 134*c* are formed to correspond respectively to the light passing hole 124*a*, the light passing hole 124*b*, and the light passing hole 124*c* of the index plate 120.

<Reflective Plate>

In FIG. 2, the reflective plate 140 is configured at the outer peripheral portion of the index plate 120 (i.e., the outer peripheral portion of the inclined portion 121B). The reflective plate 140 is a diffuse reflection surface that diffuses and reflects the illumination light emitted from the surface light emitting panel 130. The illumination light emitted from the surface light emitting panel 130 is guided to the inclined portion 121B by the reflective plate 140. The position and angle of the reflection surface of the reflective plate 140 relative to the surface light emitting panel 130 are set according to the inclination angle α (refer to FIG. 3B) of the inclined portion 121B relative to the surface light emitting panel 130. In other words, the position and angle are set so that the illumination light emitted from the surface light emitting panel efficiently enters the light-transmitting portions 122*a* formed on the inclined portion 121B, and the loss of light intensity passing through the light-transmitting portions 122*a* is minimized as much as possible (in other words, so that the pattern index is efficiently projected onto the cornea).

Further, in the case where the reflective plate 140 is provided, the size of the surface light emitting panel 130 is set to correspond to the configuration position of the reflective plate 140. In other words, the size of the surface light emitting panel 130 is made smaller compared to the case where the reflective plate 140 is not provided. This suppresses the enlargement of the size of the surface light emitting panel and allows for efficient illumination of the measurement pattern 122. Further, the enlargement of the ophthalmic device 1 itself may be suppressed.

<Adjustment of Reflection Pattern Density>

The adjustment of the density of the reflection pattern 133 formed on the back surface of the light guide plate 131 is described. As mentioned earlier, the density distribution of the reflection pattern 133 is adjusted corresponding to the positional relationship between the reflection pattern 133 and the illuminating light source 132. For example, in the case of desiring to emit light with uniform illumination intensity from the front surface of the surface light emitting panel 130, the density of the reflection pattern 133 is adjusted to become denser as the distance from the illuminating light source 132 increases. In addition, to project the measurement pattern 122 with as uniform light intensity as possible onto the examinee's eye cornea, the density of the reflection pattern 133 is adjusted corresponding to the positional relationship between the surface light emitting panel 130 and the measurement pattern 122. Furthermore, the density of the reflection pattern 133 is adjusted corresponding to the positional relationship of the measurement pattern 122 relative to the optical axis L1 of the front imaging optical system 150, and the positional relationship of the surface light emitting panel 130 relative to the optical axis L1.

Figure 6:
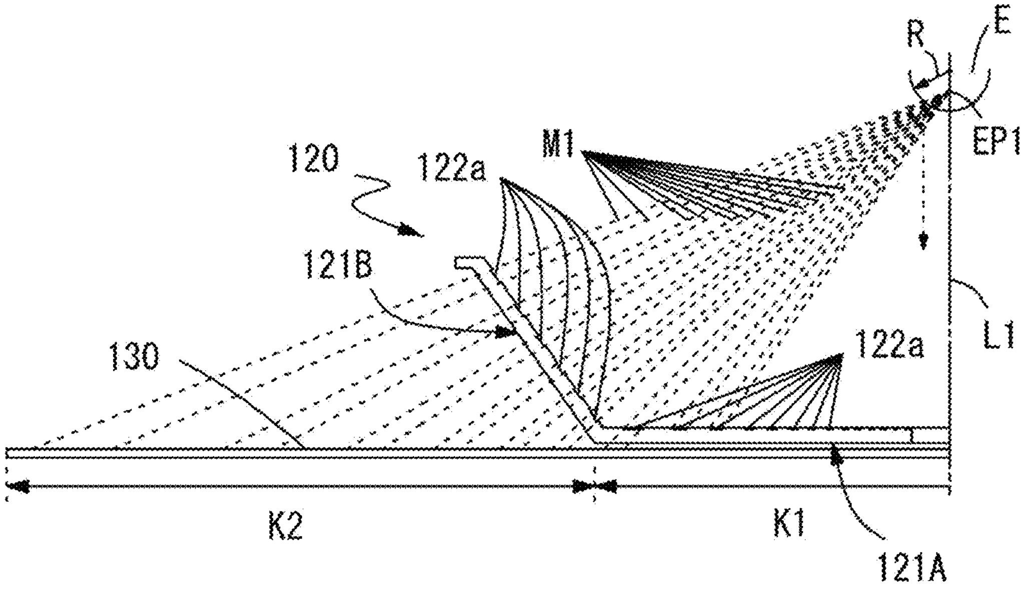
FIG. 6 is a view describing the size of the surface light emitting panel and the adjustment of the reflection pattern in the case where no reflective plate is provided.

FIG. 6 is a view describing the size of the surface light emitting panel 130 and the adjustment of the reflection pattern 133 in the case where no reflective plate 140 is provided.

The light beams that contribute to the formation of the pattern index captured by the front imaging optical system 150 are mainly considered to be the light beams M1 directed towards the point EP1, which is at a distance of ½ of the corneal curvature radius R on the optical axis L1. It is noted that the design point EP1 is set at the position where an examinee's eye with a standard corneal curvature radius R (for example, 7.8 mm) is in a completed alignment state at a predetermined working distance. Thus, in the case where the reflective plate 140 is not provided, the surface light emitting panel 130 is sized to extend to the position that emits the light beam M1 passing through the light-transmitting portion 122*a* at the outermost circumference of the measurement pattern 122. In other words, the surface light emitting panel 130 requires a size where it exists on the extension line connecting the point EP1 and the edge of the light-transmitting portion 122*a* at the outermost circumference.

Then, the inclination (the angle of inclination of light beam M1 with respect to the vertical direction of the surface light emitting panel 130) of light beam M1 contributing to the formation of the pattern index increases as the measurement pattern 122 (in this example, a ring pattern) on the index plate 120 becomes farther from the optical axis L1, as shown in FIG. 6. On the other hand, while the directionality of the light intensity of the light beam emitted from a single point on the surface light emitting panel 130 is reduced by the diffusion plate 135 configured on the front surface side, the light intensity of the light beam M1 still weakens as the inclination of the light beam M1 with respect to the vertical direction of the surface light emitting panel 130 increases. Thus, even if the light intensity viewed from the front direction (vertical direction) of the surface light emitting panel 130 is uniform across the entire front surface, as a result, the light intensity illuminating the measurement pattern 122 on the outer side away from the optical axis L1 does not become the same as the light intensity near the optical axis L1, and weakens as it moves away from the optical axis L1.

Thus, in the case where the reflective plate 140 is not configured, in order to increase the light intensity emitted from the surface light emitting panel as it moves away from the optical axis L1, the density of the reflection pattern 133 that is adjusted so that the illumination intensity emitted from the entire front surface of the surface light emitting panel 130 becomes uniform is adjusted so that the density of the reflection pattern 133 become denser as it moves away from the optical axis L1.

It is noted that regarding the domain K1 (domain on the surface light emitting panel 130) of the surface light emitting panel 130 corresponding to the flat portion 121A of the index plate 120, since it is near the optical axis L1, the inclination of the light beam M1 is not as large as the light beam M1 corresponding to the outer peripheral side on the inclined portion 121B side. Thus, in practice, the density of the reflection pattern 133 may be adjusted so that the illumination intensity emitted by the surface light emitting panel 130 is uniform. Then, in the domain K2 corresponding to the inclined portion 121B, in order to increase the light intensity emitted from the surface light emitting panel as it moves away from the optical axis L1, the density of the reflection pattern 133 may be adjusted to become denser. The adjustment amount may be experimentally determined using a model eye with a standard corneal radius.

Further, the adjustment of the density of the reflection pattern 133 in the case where the reflective plate 140 is not configured may also be applied to a case where the index plate 120 does not have an inclined portion 121B and is composed of a flat portion over its entire front surface. In this case, the index plate 120 is sized to extend to the domain K2 in FIG. 6.

Figure 7:
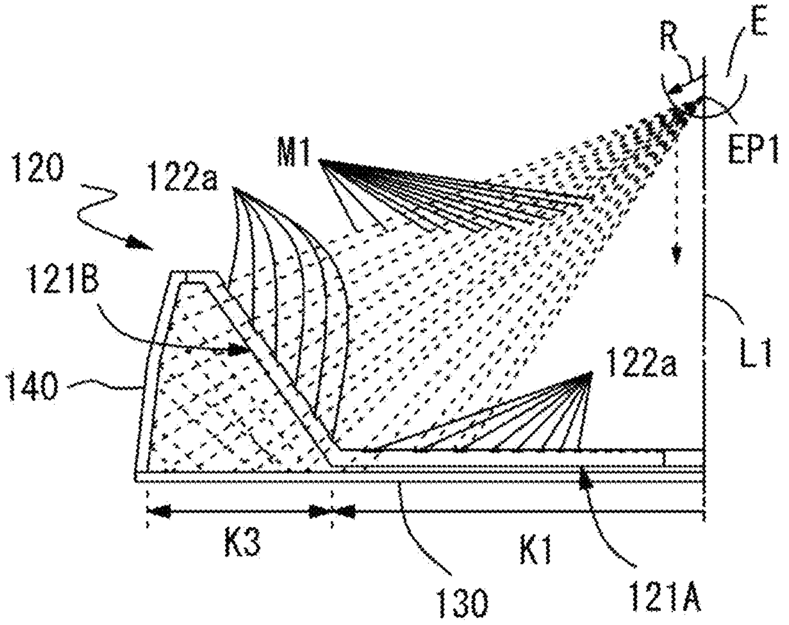
FIG. 7 is a view describing the size of the surface light emitting panel and the adjustment of the reflection pattern in the case where a reflective plate is provided.

FIG. 7 is a view describing the size of the surface light emitting panel 130 and the adjustment of the reflection pattern 133 in the case where a reflective plate 140 is provided.

In the case where the reflective plate 140 is provided at the outer peripheral portion of the inclined portion 121B, the surface light emitting panel 130 is sized to correspond to the configuration position of the reflective plate 140. The measurement pattern 122 formed on the inclined portion 121B is directly illuminated by light emitted from the surface light emitting panel 130 in the domain K3 (a domain outside the domain K1 and extending to the reflective plate 140) corresponding to the inclined portion 121B, and is also illuminated by light reflected by the reflective plate 140. For example, the light beam M1 contributing to the formation of the pattern index at the outermost circumference of the measurement pattern 122 uses a light beam with a relatively small inclination (inclination with respect to the vertical direction of the surface light emitting panel 130) among the light beams generated in all directions from the surface light emitting panel 130 due to the reflection by the reflective plate 140. Thus, compared to the case in FIG. 6 (where the reflective plate 140 is not provided), the light intensity illuminating the measurement pattern 122 formed on the inclined portion 121B becomes stronger. Further, the light emitted from the domain K3 of the surface light emitting panel 130 is reflected and diffused on the back surface of the inclined portion 121B, directed towards the reflective plate 140, and further reflected by the reflective plate 140 to illuminate the measurement pattern 122. As a result, the light intensity illuminating the measurement pattern 122 formed on the inclined portion 121B becomes even stronger. Consequently, in the case where the light intensity is uniform across the entire front surface when viewing the surface light emitting panel 130 from the front direction (vertical direction), the illumination intensity of the measurement pattern 122 on the inclined portion 121B becomes relatively stronger compared to the illumination intensity of the flat portion 121A.

Thus, in the case where the reflective plate 140 is configured, the density of the reflection pattern 133 is adjusted so that the light intensity emitted from the domain K3 becomes relatively weaker compared to the light intensity emitted from the domain K1. In other words, the density of the reflection pattern 133 is adjusted so that the illumination intensity on the front surface (domain K3) of the surface light emitting panel 130 corresponding to the measurement pattern 122 formed on the inclined portion 121B becomes relatively weaker compared to the illumination intensity on the front surface (domain K1) of the surface light emitting panel 130 corresponding to the flat portion 121A. As a result, in the configuration where the reflective plate 140 is configured on the outer peripheral side of the inclined portion 121B, both the measurement pattern 122 on the flat portion and the measurement pattern 122 on the inclined portion of the index plate 120 may be uniformly illuminated with approximately the same light intensity.

Further, the density of the reflection pattern 133 of the surface light emitting panel 130 may be adjusted according to the formation position of the light passing holes (134*a*, 134*b*, 134*c*) shown in FIG. 5. The illuminating light source 132 of the surface light emitting panel 130 is configured at the end portion of the light guide plate 131, and the illumination light from the illuminating light source 132 is guided to the center side of the light guide plate 131. Thus, when holes are formed in the middle of the light guide plate 131, the illumination light from the illuminating light source 132 becomes difficult to be guided to the rear part around the light passing holes (134*a*, 134*b*, 134*c*) as viewed from the illuminating light source 132 side. As a result, illumination unevenness is likely to occur near the light passing holes (134*a*, 134*b*, 134*c*) corresponding to that rear part. To resolve this, the density of the reflection pattern 133 in the rear part of the light passing holes is adjusted to be denser compared to the front part of the light passing holes, as viewed from the illuminating light source 132 side. It is noted that the illumination unevenness associated with the position of the light passing holes differs depending on the position and distance relative to the illuminating light sources 132 configured on each side of the end portion of the surface light emitting panel 130, so the density of the reflection pattern 133 may actually be adjusted through experimentation.

<Front Imaging Optical System>

The front imaging optical system 150 includes an objective lens 151, an imaging lens 152, and an image-pickup element 153 on the optical axis L1 for measurement. For example, the image-pickup element 153 is configured at a position conjugate with the pupil of the examinee's eye anterior ocular segment. During the cornea shape measurement, the front imaging optical system 150 is used to capture an index image formed by the pattern index projected onto the cornea of the examinee's eye. Further, a front image of the examinee's eye anterior ocular segment illuminated by the anterior ocular segment illuminating light source 155 is captured by the image-pickup element 153. Further, the front imaging optical system 150 also serves as a detection optical system for detecting the index image projected onto the examinee's eye cornea by the front alignment index projection optical system 170. The index image formed by the front alignment index projection optical system 170 is captured by the image-pickup element 153. A color camera may be used as the image-pickup element 153.

<Working Distance Detection Optical System>

The working distance detection optical system 160 includes a light projecting optical system 161 and a light receiving optical system 165. The light projecting optical system 161 includes a light source 162 that emits infrared light and a lens 163. The light receiving optical system 165 includes a lens 166 and a light receiving element 167. The working distance detection optical system 160 is used to align the optometry unit 10 in the working distance direction (Z direction) with respect to the examinee's eye.

The light from the light source 162 is collimated into a substantially parallel light beam by the lens 163, and is projected onto the cornea of the examinee's eye at an oblique angle through the light passing holes 134*b* formed in the surface light emitting panel 130 and the light passing holes 124*b* formed in the index plate 120. The optical axis of the light receiving optical system 165 is configured symmetrically to the optical axis of the light projecting optical system 161 with respect to the optical axis L1. The corneal reflection light from the light projecting optical system 161 enters the light receiving element 167 through the light passing holes 124*b* formed in the index plate 120, the light passing holes 134*b* formed in the surface light emitting panel 130, and the lens 166. In response to the examinee's eye moving relatively in the working distance direction (Z direction), the index image (image of the light source 162) formed on the examinee's eye cornea also moves on the light receiving element 167. Thus, by detecting the index image on the light receiving element 167, the alignment state of the optometry unit 10 in the working distance direction with respect to the examinee's eye is detected.

<Front Alignment Index Projection Optical System>

The front alignment index projection optical system 170 includes a light source 171 that emits infrared light, a second index plate 172, a lens 173, and a half mirror 174. For example, a ring index is formed on the second index plate 172. The light beam of the ring index on the second index plate 172 illuminated by the light source 171 is made coaxial with the optical axis L1 by the half mirror 174 through the lens 173, and is projected onto the cornea of the examinee's eye, thereby forming a ring index image on the examinee's eye cornea. The ring index image projected on the examinee's eye cornea is imaged by the image-pickup element 153 of the front imaging optical system 150. Then, by processing the ring image captured by the image-pickup element 153, the alignment state in the X and Y directions of the relative positional relationship between the examinee's eye and the optometry unit 10 is detected.

It is noted that, for example, a double ring index is formed on the second index plate 172. During cornea shape measurement, the front alignment index projection optical system 170 is also used as an optical system for projecting an internal pattern index for cornea shape measurement.

<Fixation Target Presentation Optical System>

The fixation target presentation optical system 180 presents a fixation target to the examinee's eye. The fixation target presentation optical system 180 includes at least a light source 181 that emits visible light and a fixation target plate 182. The fixation light beam from the light source 181 passes through the fixation target plate 182, lens 183, half mirror 184, and lens 185, and is then reflected by the half mirror 186 to be made coaxial with the optical axis L1. Subsequently, the fixation light beam reaches the fundus of the examinee's eye through the lens 151.

<Cross-Sectional Imaging Optical System>

The cross-sectional imaging optical system 210 is used to capture a cross-sectional image of the anterior ocular segment. The cross-sectional imaging optical system 210 includes a light projecting optical system 210*a* and a light receiving optical system 210*b*.

The light projecting optical system 210*a* is made coaxial with the optical axis L1 and projects slit light, which is an example of imaging light, onto the anterior ocular segment. The light projecting optical system 210*a* includes a light source 211, a slit 212 and the like. For example, for the light source 211, red visible light or near-infrared light is used as the imaging light. The slit 312 may be configured at a position conjugate to the pupil. For example, the slit 212 is configured so that the slit light performs light cutting in the horizontal direction (X direction) of the anterior ocular segment.

The light receiving optical system 210*b* includes a lens system 222 and an image-pickup element 221, which is an example of a light detector, and the like. In the light receiving optical system 210*b*, the lens system 222 and the image-pickup element 221 are configured in a Scheimpflug relationship with the cross-section set in the anterior ocular segment. In other words, the optical configuration is such that the extended planes of the cross-section, the principal plane of the lens system 222, and the imaging surface of the image-pickup element 221 intersect at a single line of intersection (single axis). The image-pickup element 221 receives return light (reflected light or scattered light) from the anterior ocular segment that has been light-cut by the slit light. Then, based on the signal from the image-pickup element 221, a cross-sectional image of the anterior ocular segment is obtained.

In the cross-sectional imaging optical system 210, the imaging light beam from the light source 211 becomes a slit light beam through the slit 212, passes through the lens 213, half mirror 184, and lens 185, and is then reflected by the half mirror 186 to be made coaxial with the optical axis L1. Subsequently, the imaging light beam reaches the anterior ocular segment through the objective lens 174. The return light from the cross-section formed in the anterior ocular segment reaches the image-pickup element 221 through the light passing hole 124*a* formed in the index plate 120, the light passing hole 134*a* formed in the surface light emitting panel 130, and the lens system 222. As a result, a cross-sectional image of the examinee's eye anterior ocular segment is obtained.

<Control System>

In FIG. 2, the controller 50 controls the overall operation of the ophthalmic device 1. The controller 50 is connected to various electrical components such as the image-pickup element 150, the image-pickup element 221, light sources of the optical systems, the monitor 16, and the alignment driving portion 13. Further, the controller 50 also functions as an image processor that processes images captured by the image-pickup element 153 and the image-pickup element 221. For example, during cornea shape measurement, the controller 50 processes images of index images projected onto the examinee's eye cornea and analyzes the cornea shape of the examinee's eye cornea according to a predetermined program. Further, the controller 50 obtains the cross-sectional image of the anterior ocular segment captured by the image-pickup element 221 and analyzes it according to a predetermined program to obtain the shape of the anterior ocular segment tissue.

The monitor 16 functions as a touch panel that also serves as an operation unit. Further, the monitor 16 displays measurement results of the examinee's eye (such as the anterior ocular segment cross-sectional image, cornea shape measurement results, etc.) on its screen. Further, the controller 50 is connected to a memory 52, which is an example of a storage device. The memory 52 stores the front anterior ocular segment image obtained by the image-pickup element 150, the anterior ocular segment cross-sectional image obtained by the image-pickup element 221, measurement results, and other data. Further, various control programs are also stored in the memory 52.

<Control Operation>

The operation of the ophthalmic device 1 having the above-described configuration is briefly described.

(Alignment)

When the examinee's face is supported by the face supporting unit 15, an illuminated image of the examinee's eye illuminated by the anterior ocular segment illuminating light source 155 is captured by the front imaging optical system 150, and an anterior ocular segment image is displayed on the monitor 16. The controller 50 processes the front image of the anterior ocular segment obtained by the front imaging optical system 150, and detects the XY-direction alignment state of the optometry unit 10 (optical axis L1) with respect to the corneal apex based on the index (corneal reflection bright point) projected onto the examinee's eye cornea by the front alignment index projection optical system 170. Further, the controller 50 detects the Z-direction alignment state based on the output of the light receiving element 167 of the working distance detection optical system 160. Then, the controller 50 controls the driving of the alignment driving portion 13 and moves the optometry unit 10 in the XYZ directions so that the alignment state in the XYZ directions falls within a predetermined acceptable range, respectively.

(Cornea Shape Measurement)

In response to the completion of alignment, the illuminating light source 132 of the surface light emitting panel 130 is turned on, and a pattern index is projected onto the examinee's eye cornea through the index plate 120. The cornea reflection image of the pattern index is captured by the image-pickup element 153 of the front imaging optical system 150 and stored in the memory 52. The controller 50 obtains a detailed shape map of the corneal anterior surface by processing and analyzing the cornea reflection image of the pattern index. At this time, the measurement pattern 122 is uniformly (substantially uniformly) illuminated by the illumination light from the surface light emitting panel 130, thereby reducing illumination unevenness of the pattern index on the cornea. This allows for good capture of the cornea reflection image of the pattern index. As a result, the cornea shape may be measured with high accuracy. The measurement result of the cornea shape is displayed, for example, as a shape map on the monitor 16.

(Measurement of Anterior Ocular Segment Cross-Sectional Shape)

Next, the alignment state of the optometry unit 10 with respect to the examinee's eye is confirmed, and a cross-sectional image of the examinee's eye anterior ocular segment is captured in the completed alignment state. When the light source 211 of the cross-sectional imaging optical system 210 is turned on, the examinee's eye anterior ocular segment is light-cut by slit light from the slit 212. The controller 50 obtains a cross-sectional image of the anterior ocular segment as the return light from the light-cut anterior ocular segment is captured by the image-pickup element 221. The controller 50 processes and analyzes the cross-sectional image, for example, to obtain the positions of the corneal anterior surface and the corneal posterior surface of the corneal tissue. The analysis result is displayed on the monitor 16 along with the cross-sectional image.

What is claimed is:

1. An ophthalmic device, for measuring a cornea shape of an examinee's eye, comprising:

- a surface light emitting panel in a flat plate shape, comprising:
  - a light guide plate in a flat plate shape, the light guide plate having a back surface on which a reflection pattern is formed to reflect illumination light guided inside the light guide plate and a front surface from which the illumination light reflected by the reflection pattern is emitted; and
  - an illuminating light source, configured on a side surface of the light guide plate to irradiate the illumination light inside the light guide plate;
- an index plate, on which a measurement pattern is formed and forming a pattern index to be projected onto a cornea of the examinee's eye by passing illumination light from the surface light emitting panel through the measurement pattern;
- an imaging optical system, capturing an index image which is a cornea reflection image of the pattern index; and
- an image processor, obtaining information related to the cornea shape of the examinee's eye by performing analysis processing on the index image,
- wherein a density of the reflection pattern at each position of the surface light emitting panel is set based on a positional relationship between the surface light emitting panel and the measurement pattern.

2. The ophthalmic device according to claim 1, wherein at least one of the reflection pattern and the measurement pattern is formed relative to a photographic optical axis of the imaging optical system.

3. The ophthalmic device according to claim 1, wherein the index plate comprises an inclined portion inclined with respect to the surface light emitting panel, a reflective plate is configured on an outer peripheral side of the inclined portion to guide illumination light to the measurement pattern on the inclined portion by reflecting the illumination light emitted from the surface light emitting panel, and the surface light emitting panel has a size corresponding to a configuration position of the reflective plate.

4. The ophthalmic device according to claim 3, wherein the index plate comprises a flat portion centered on a photographic optical axis of the imaging optical system, the inclined portion is configured on an outer peripheral side of the flat portion, and the density of the reflection pattern is set such that an illumination intensity on a front surface of the surface light emitting panel corresponding to the measurement pattern formed on the inclined portion is relatively weaker compared to an illumination intensity on a front surface of the surface light emitting panel corresponding to the flat portion.

5. The ophthalmic device according to claim 1, wherein the surface light emitting panel has a light passing hole formed to allow at least one of a light beam used for alignment or a light beam used for measuring optical characteristics of the examinee's eye other than a cornea shape measurement to pass through, and the density of the reflection pattern is set according to a formation position of the light passing hole.

6. The ophthalmic device according to claim 1, wherein the surface light emitting panel, when viewed from a front direction where the examinee's eye is positioned, is formed into a polygon corresponding to a shape of the index plate and has more sides than a quadrilateral, and the illuminating light source is configured on each side of the polygon.

* * * * *